(12) United States Patent
Boisart et al.

(10) Patent No.: US 10,124,512 B2
(45) Date of Patent: Nov. 13, 2018

(54) METHOD FOR RECYCLING PLASTIC PRODUCTS

(71) Applicant: CARBIOS, Saint-Beauzire (FR)

(72) Inventors: Cédric Boisart, Fontaine-Mâcon (FR); Emmanuel Maille, Ennezat (FR)

(73) Assignee: CARBIOS, Saint-Beauzire (FR)

( * ) Notice: Subject to any disclaimer, the term of this patent is extended or adjusted under 35 U.S.C. 154(b) by 0 days.

(21) Appl. No.: 14/443,524

(22) PCT Filed: Nov. 19, 2013

(86) PCT No.: PCT/EP2013/074173
§ 371 (c)(1),
(2) Date: May 18, 2015

(87) PCT Pub. No.: WO2014/079844
PCT Pub. Date: May 30, 2014

(65) Prior Publication Data
US 2015/0290840 A1     Oct. 15, 2015

(30) Foreign Application Priority Data
Nov. 20, 2012  (EP) ..................... 12306442

(51) Int. Cl.
| C08J 11/10 | (2006.01) |
| B29B 17/00 | (2006.01) |
| B29B 17/04 | (2006.01) |
| C12P 7/44 | (2006.01) |
| C12P 7/56 | (2006.01) |
(Continued)

(52) U.S. Cl.
CPC .......... B29B 17/00 (2013.01); B29B 17/0412 (2013.01); C08J 11/105 (2013.01); C12P 7/44 (2013.01); C12P 7/56 (2013.01); B29K 2101/12 (2013.01); B29K 2105/26 (2013.01); C08J 2367/04 (2013.01); C08J 2377/00 (2013.01); Y02W 30/702 (2015.05)

(58) Field of Classification Search
None
See application file for complete search history.

(56) References Cited

U.S. PATENT DOCUMENTS

| 6,312,578 B1 | 11/2001 | Canivenc et al. |
| 2015/0056673 A1 | 2/2015 | Boisart |

FOREIGN PATENT DOCUMENTS

| EP | 1 548 053 | 6/2005 |
| EP | 2 348 122 | 7/2011 |
(Continued)

OTHER PUBLICATIONS

Ronkvist et al., Macromolecules 42: 5128-5138 (2009).*
(Continued)

*Primary Examiner* — Erin M. Bowers
(74) *Attorney, Agent, or Firm* — Saliwanchik, Lloyd & Eisenschenk

(57) ABSTRACT

The invention relates to a method for recycling at least one plastic product, the method comprising degrading at least one polymer of the plastic product to monomers using an enzyme and recovering the resulting monomers. The method of the invention may be used for degrading, simultaneously or sequentially, at least two different polymers of the plastic product, and/or for recycling at least two plastic products.

23 Claims, 2 Drawing Sheets

Specification includes a Sequence Listing.

(51) Int. Cl.
*B29K 101/12* (2006.01)
*B29K 105/26* (2006.01)

(56) References Cited

FOREIGN PATENT DOCUMENTS

| | | | |
|---|---|---|---|
| EP | 2348122 | * | 7/2011 |
| JP | 2000-506442 | | 5/2000 |
| JP | 2002-320499 | | 11/2002 |
| JP | 2003-079388 | | 3/2003 |
| JP | 2004-290130 | | 10/2004 |
| WO | WO 2005/026245 | | 3/2005 |
| WO | WO 2013/144239 | | 10/2013 |

OTHER PUBLICATIONS

Chen et al., J. Biol. Chem. 283(38): 25854-25862 (2008).*
Kyrikou et al., J. Polym. Environ. 15: 125-150 (2007).*
Demirel et al., BAÜ Fen Bil. Enst. Dergisi Cilt 13(1): 26-35 (2011).*
Yoshida et al., Science 351(6278): 1196-1199 (2016).*
Bartolome et al., "Recent Developments in the Chemical Recycling of PET", Material Recycling—Trends and Perspectives, InTech, published Mar. 16, 2012.*
Nabil et al., J. Elastomers Plastics 00-2011: 1-21 (2011).*
Currently pending claims of U.S. Appl. No. 14/387,285, filed 2014, pp. 1-3.
Database WPI, Accession No. 2005-262580, Mar. 24, 2005, pp. 1-3, XP-002690554.
Database WPI, Accession No. 2004-751104, Oct. 21, 2004, pp. 1-2, XP-002690555.

* cited by examiner

METHOD FOR RECYCLING PLASTIC PRODUCTS

CROSS-REFERENCE TO RELATED APPLICATION

This application is the U.S. national stage application of International Patent Application No. PCT/EP2013/074173, filed Nov. 19, 2013.

The present invention relates to a method for recycling plastic products, such as waste plastics. More particularly, the invention relates to a biological method for depolymerizing at least one polymer of a plastic product and recovering the resulting monomers, which may be further reprocessed for synthesizing new polymers and manufacturing new plastic products.

CONTEXT OF THE INVENTION

Plastics are inexpensive and durable materials, which can be used to manufacture a variety of products that find use in a wide range of applications, so that the production of plastics has increased dramatically over the last decades. About 40% of these plastics are used for single-use disposable applications, such as packaging, agricultural films, and disposable consumer items, or for short-lived products that are discarded within a year of manufacture. Because of the durability of the polymers involved, substantial quantities of plastics are piling up in landfill sites and in natural habitats worldwide, generating increasing environmental problems. Even degradable and biodegradable plastics may persist for decades depending on local environmental factors, like levels of ultraviolet light exposure, temperature, presence of suitable microorganisms, etc.

One solution to reduce environmental and economic impacts correlated with the accumulation of plastic is closed-loop recycling, wherein plastic material is mechanically reprocessed to manufacture new products. For example, one of the most common types of closed-loop recycling is polyethylene terephthalate (PET) recycling. PET wastes are subjected to successive treatments leading to food-contact-approved recycled PET (rPET), which is collected, sorted, pressed into bales, crushed, washed, chopped into flakes, melted and extruded in pellets and offered for sale. Then this recycled PET may be used to create fabrics for the clothing industry or new packaging such as bottles, blister packs, etc.

However, plastic wastes are generally collected all together, so that plastic bales contain a mixture of different plastics, the composition of which may vary from source to source, and the proportions of which may vary from bale to bale. Consequently, recycling processes require preliminary selection to sort out the plastic products according to their composition, size, resin type, color, functional additives used, etc.

In addition, the actual plastic recycling processes use huge amounts of electricity, particularly during the extruding step, and the equipment used is also expensive, leading to high prices which may be non-competitive compared to virgin plastic.

Another potential process for recycling plastic consists of chemical recycling, allowing recovery of the chemical constituents of the polymer. The resulting monomers may then be used to re-manufacture plastic or to make other synthetic chemicals. However, up to now, such a recycling process has only been performed on purified polymers and is not efficient on raw plastic products constituted of a mix of crystallized and amorphous polymers and additives.

Thus, a need exists for an upgraded process for recycling plastic products that does not require preliminary sorting and expensive pretreatments and that may be used for recycling different plastic materials.

SUMMARY OF THE INVENTION

The inventors now propose a biological process for depolymerizing at least one polymer of at least one plastic product with low energy consumption. The process of the invention allows recovery of the monomers that formed the original polymers of a plastic product, so that said monomers may be reprocessed to synthesize new polymer chains of the same type. More particularly, the inventors propose to use particular enzymes which are able to depolymerize polymer(s) of said plastic product and yield a mix of monomers that formed the original polymer(s).

In this regard, it is an object of the invention to propose a method for recycling at least one plastic product, comprising depolymerizing at least one polymer of the plastic product to monomers using an enzyme and recovering the resulting monomers.

A further object of the invention relates to a method for recycling at least two different polymers of a plastic product, wherein said at least two different polymers are depolymerized, simultaneously or sequentially, and wherein the resulting monomers are recovered.

The invention also concerns a method for recycling, simultaneously or sequentially, at least two different plastic products, wherein at least one polymer of each plastic product is degraded to monomers using at least one enzyme, and wherein the resulting monomers are recovered.

Preferably, the plastic product comprises at least one polymer chosen among polyesters and polyamides.

More preferably, the polyester is selected from polyethylene terephthalate (PET), polytrimethylene terephthalate (PTT), polybutylene terephthalate (PBT), polyethylene isosorbide terephthalate (PEIT), polylactic acid (PLA), poly (L-lactic acid) (PLLA), poly(D-lactic acid) (PDLA), poly (D,L-lactic acid) (PDLLA), PLA stereocomplex (scPLA), polyhydroxy alkanoate (PHA), poly(3-hydroxybutyrate) (P(3HB)/PHB), poly(3-hydroxyvalerate) (P(3HV)/PHV), poly(3-hydroxyhexanoate) (P(3HHx)), poly(3-hydroxyoctanoate) (P(3HO)), poly(3-hydroxydecanoate) (P(3HD)), poly(3-hydroxybutyrate-co-3-hydroxyvalerate) (P(3HB-co-3HV)/PHBV), poly(3-hydroxybutyrate-co-3-hydroxyhexanoate) (P(3HB-co-3HHx)/(PHBHHx)), poly(3-hydroxybutyrate-co-5-hydroxyvalerate) (PHB5HV), poly(3-hydroxybutyrate-co-3-hydroxypropionate) (PHB3HP), polyhydroxybutyrate-co-hydroxyoctonoate (PHBO), polyhydroxybutyrate-co-hydroxyoctadecanoate (PHBOd), poly (3-hydroxybutyrate-co-3-hydroxyvalerate-co-4-hydroxybutyrate) (P(3HB-co-3HV-co-4HB)), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA) and blends/mixtures of these materials.

The polyamide is preferably selected from polyamide-6 or poly(β-caprolactam) or polycaproamide (PA6), polyamide-6,6 or poly(hexamethylene adipamide) (PA6,6), poly(11-aminoundecanoamide) (PA11), polydodecanolactam (PA12), poly(tetramethylene adipamide) (PA4,6), poly(pentamethylene sebacamide) (PA5,10), poly(hexamethylene azelaamide) (PA6,9), poly(hexamethylene sebacamide) (PA6,10), poly(hexamethylene dodecanoamide) (PA6,12), poly(m-xylylene adipamide) (PAMXD6), polyhexamethylene adipamide/polyhexamethylene terephthalamide copolymer (PA66/6T), polyhexamethylene adipamide/polyhexamethylene isophthalamide copolymer (PA66/6I) and blends/mixtures of these materials.

Advantageously, the recovered monomers are further reprocessed to synthesize new polymer(s).

Preferably, the enzyme is a degrading enzyme suitable for depolymerizing at least one polymer of the plastic product to monomers.

The degrading enzyme is preferably selected from cutinase (EC 3.1.1.74), lipase (EC 3.1.1.3), esterase, carboxylesterase (EC 3.1.1.1), p-nitrobenzylesterase, serine protease (EC 3.4.21.64), protease, amidase, aryl-acylamidase (EC 3.5.1.13), oligomer hydrolase such as 6-aminohexanoate cyclic dimer hydrolase (EC 3.5.2.12), 6-aminohexanoate dimer hydrolase (EC 3.5.1.46), 6-aminohexanoate-oligomer hydrolase (EC 3.5.1.B17), peroxidase, and laccase (EC 1.10.3.2).

In another particular embodiment, the enzyme may be an intermediate enzyme producing and/or activating at least one intermediate molecule suitable for depolymerizing at least one polymer of the plastic product to monomers.

In a particular embodiment, the method comprises the following steps:
a) Contacting the plastic product with at least one microorganism expressing and excreting the depolymerase or intermediate enzyme; and
b) Recovering the monomers resulting from depolymerization of at least one polymer of said plastic product.

In a particular embodiment, the microorganism expressing and excreting said enzyme is a recombinant microorganism with a modified metabolism preventing the consumption of the resulting monomers.

In a further particular embodiment, the microorganism is a recombinant microorganism expressing and excreting a recombinant degrading enzyme.

In another particular embodiment, the method comprises the following steps:
a) Contacting the plastic product with at least one depolymerizing enzyme; and
b) Recovering the monomers resulting from depolymerization of at least one polymer of said plastic product.

According to the invention, the degrading enzyme may be used with at least one lipophilic and/or hydrophilic agent.

The plastic product may be pretreated prior to degradation. More particularly, the pretreatment may include a mechanical/physical modification of the plastic product, like cutting and impact, crushing and grinding, fractionation, cryogenic cooling step, dessicating, dehydration, agglomeration, or granulation.

In a particular embodiment, the plastic products may be further sorted, washed and/or biologically cleaned prior to degradation.

These and the other objects and embodiments of the invention will become more apparent after the detailed description of the invention, including preferred embodiments thereof given in general terms.

DETAILED DESCRIPTION OF THE INVENTION

Figure 1:
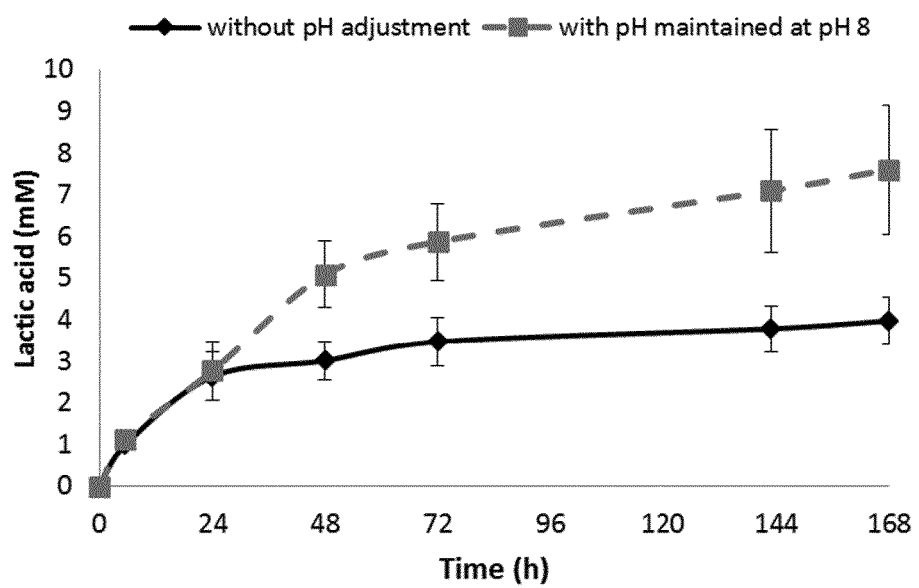
FIG. 1 shows the production of lactic acid following the hydrolysis of polylactic acid polymer contained in plastic pellets according to the process of the invention. The adjustment of the pH to maintain it around 8 allows the monomer production to be increased after even 48 h or 72 h.

The present invention refers to a complete recycling process for recycling a plastic product by depolymerizing at least one polymer constituting said plastic product, wherein a repolymerizable monomer mixture is generated and recovered.

Definitions

The present disclosure will be best understood by reference to the following definitions.

Within the context of the invention, the term "plastic product" refers to any item made from at least one plastic material, such as plastic sheet, tube, rod, profile, shape, massive block, fiber, etc., which contains at least one polymer, and possibly other substances or additives, such as plasticizers or mineral or organic fillers. Preferably the plastic product is constituted of a mix of semi-crystalline and/or amorphous polymers, or semi-crystalline polymers and additives. More preferably, the plastic product is a manufactured product like packaging, agricultural films, disposable items or the like. The plastic materials of the invention include synthetic, degradable and biodegradable plastics. Within the context of the invention, natural and synthetic rubbers are not considered as plastic material, and rubber products are excluded from the scope of the invention.

A "polymer" refers to a chemical compound or mixture of compounds whose structure is constituted of multiple repeating units linked by covalent chemical bonds. Within the context of the invention, the term "polymer" includes natural or synthetic polymers, constituted of a single type of repeat unit (i.e., homopolymers) or of a mixture of different repeat units (i.e., block copolymers and random copolymers).

A "recycling process" in relation to a plastic product refers to a process by which at least one polymer of said plastic product is degraded to yield repolymerizable monomers, which are retrieved in order to be reused.

In the present description, a "recombinant microorganism" refers to a microorganism whose genome has been modified by insertion of at least one nucleic acid sequence or unit. Typically, the inserted nucleic acid sequence or unit is not naturally present in the genome of the microorganism. Said nucleic acid sequence or unit has been assembled and/or inserted in said microorganism or an ancestor thereof using recombinant DNA technology (also called gene cloning or molecular cloning), which refers to techniques of transfer of DNA from one organism to another. The nucleic acid sequence or unit may be intergrated into the microbial chromosome, or present on a plasmid. A "recombinant microorganism" further refers to a microorganism whose genome has been modified by inactivation or deletion of at least one nucleic acid sequence or unit. The resulting recombinant microorganism can be manufactured by a variety of methods, and, once made, can be reproduced without use of further recombinant DNA technology. Otherwise, the recombinant microorganism may be issued from a metagenomic library.

The terms "nucleic acid", "nucleic sequence", "polynucleotide", "oligonucleotide" and "nucleotide sequence" are used interchangeably and refer to a sequence of deoxyribonucleotides and/or ribonucleotides. The nucleotide sequence may be first prepared by, e.g., recombinant, enzymatic and/or chemical techniques, and subsequently replicated in a host cell or an in vitro system. The nucleotide sequence preferentially comprises an open reading frame encoding a (poly)peptide. The nucleotide sequence may contain additional sequences such as a transcription terminator, a signal peptide, an intron, etc.

Within the context of the invention, the term "derived from a microorganism" in relation to an enzyme or (poly) peptide indicates that the enzyme or (poly)peptide has been isolated from such a microorganism, or that the enzyme or (poly)peptide comprises all or a biologically active part of the amino acid sequence of an enzyme or (poly)peptide isolated or characterized from such a microorganism.

The term "vector" refers to DNA molecule used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally an operator.

Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well-known in the art. Bacterial expression vectors well-known in the art include pET11a (Novagen) and lambda gt11 (Invitrogen).

Expression vectors may be introduced into host cells using standard techniques. Examples of such techniques include transformation, transfection, lipotransfection, protoplast fusion, and electroporation. Examples of techniques for introducing a nucleic acid into a cell and expressing the nucleic acid to produce protein are provided in references such as Ausubel, Current Protocols in Molecular Biology, John Wiley, 1987-1998, and Sambrook et al., in Molecular Cloning: A Laboratory Manual, $2^{nd}$ Edition, Cold Spring Harbor Laboratory Press, 1989.

Plastic Products

The present invention proposes to degrade plastic products up to the monomer level, so that said monomers may be reused for repolymerizing polymers and further fabricating new plastic products.

The method of the invention may be used for recycling plastic products made with several different plastic materials. For example the plastic product may comprise successive layers of different plastic materials.

The recycling process of the invention may be used for degrading all kinds of plastic products, without the necessity of preliminary plastic sorting and/or cleaning. More particularly, the process of the invention may be directly applied to plastic products coming from plastic waste collection. For example, the process of the invention may be applied to a mix of domestic plastic wastes, including plastic bottles, plastic bags, plastic packaging, textile waste, etc.

The plastic products targeted by the process of the invention may comprise different kinds of plastic materials, including synthetic plastic materials, derived from petrochemicals, or biobased plastic materials (i.e., composed in whole or significant part of biological products).

The targeted plastic products may contain one or several polymers and additives. One plastic product may be made up of several kinds of polymers arranged in different layers or melted together. Furthermore, the plastic product may be constituted of semi-crystalline polymers or a mix of semi-crystalline and amorphous polymers as well as additives.

In a particular embodiment, the plastic product only consists of polymers containing a main saturated linear carbon chain, which may further contain saturated or unsaturated cycle(s), such as an aromatic cycle.

In a particular embodiment, the targeted plastic products comprise polyesters and/or polyamides. Preferably, the plastic products contain only polyesters and/or polyamides. Preferred polyesters are polyethylene terephthalate (PET), polytrimethylene terephthalate (PTT), polybutylene terephthalate (PBT), polyethylene isosorbide terephthalate (PEIT), polylactic acid (PLA), poly(L-lactic acid) (PLLA), poly(D-lactic acid) (PDLA), poly(D,L-lactic acid) (PDLLA), PLA stereocomplex (scPLA), polyhydroxy alkanoate (PHA), poly(3-hydroxybutyrate) (P(3HB)/PHB), poly(3-hydroxyvalerate) (P(3HV)/PHV), poly(3-hydroxyhexanoate) (P(3HHx)), poly(3-hydroxy octanoate) (P(3HO)), poly(3-hydroxydecanoate) (P(3HD)), poly(3-hydroxybutyrate-co-3-hydroxyvalerate) (P(3HB-co-3HV)/PHBV), poly(3-hydroxybutyrate-co-3-hydroxyhexanoate) (P(3HB-co-3HHx)/(PHBHHx)), poly(3-hydroxybutyrate-co-5-hydroxyvalerate) (PHB5HV), poly(3-hydroxybutyrate-co-3-hydroxypropionate) (PHB3HP), polyhydroxybutyrate-co-hydroxyoctonoate (PHBO), polyhydroxybutyrate-co-hydroxyoctadecanoate (PHBOd), poly(3-hydroxybutyrate-co-3-hydroxyvalerate-co-4-hydroxybutyrate) (P(3HB-co-3HV-co-4HB)), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA) and blends/mixtures of these materials, and preferred polyamides are polyamide-6 or poly(ε-caprolactam) or polycaproamide (PA6), polyamide-6,6 or poly (hexamethylene adipamide) (PA6,6), poly(11-aminoundecanoamide) (PA11), polydodecanolactam (PA12), poly (tetramethylene adipamide) (PA4,6), poly(pentamethylene sebacamide) (PA5,10), poly(hexamethylene azelaamide) (PA6,9), poly(hexamethylene sebacamide) (PA6,10), poly (hexamethylene dodecanoamide) (PA6,12), poly(m-xylylene adipamide) (PAMXD6), polyhexamethylene adipamide/polyhexamethylene terephthalamide copolymer (PA66/6T), polyhexamethylene adipamide/polyhexamethylene isophthalamide copolymer (PA66/6I) and blends/mixtures of these materials.

In a particular embodiment, the plastic product is constituted of aliphatic polyester, such as polylactic acid, and more particularly semi-crystalline polylactic acid.

In another embodiment, the plastic product is constituted of aromatic polyester, such as polyethylene terephthalate and/or polytrimethylene terephthalate, more particularly semi-crystalline ones.

Plastic Degradation

It is an object of the present invention to provide degrading enzymes suitable for hydrolyzing chemical bonds between monomers of at least one polymer of a plastic product.

According to the invention, such degrading enzymes may be cutinase, lipase, esterase, carboxylesterase, p-nitrobenzylesterase, serine protease, protease, amidase, aryl-acylamidase, oligomer hydrolase, peroxidase, laccase, etc., depending on the polymer to be hydrolyzed.

For example, serine protease (like the proteinase K from *Tritirachium album* or PLA depolymerase from *Amycolatopsis* sp.), lipase (like the one from *Candida antarctica* or *Cryptococcus* sp. or *Aspergillus niger*) or esterase (like the one from *Thermobifida halotolerans*) may be used for depolymerizing a plastic product containing polylactic acid (PLA). A cutinase (like the one from *Thermobifida fusca, Thermobifida alba* or *Fusarium solani pisi*) or a lipase (like the lipase PS from *Burkholderia cepacia*) may be used for depolymerizing a plastic product containing PET or PTT. A cutinase (like the one from *Fusarium solani*), an aryl-acylamidase (like the one from *Nocardia farcinica*), an oligomer hydrolase (like the 6-aminohexanoate oligomer hydrolase from *Arthrobacter* sp.) or an amidase (like the one from *Beauveria brongniartii*) may be used for depolymerizing a plastic product containing PA6 or PA6,6.

In a particular embodiment, the plastic product to be recycled is contacted with the degrading enzyme, which may be natural or synthetic.

For example, the degrading enzyme may be produced by recombinant techniques, or it may be isolated or purified from natural sources, when naturally-occurring, or it may be artificially produced. The enzyme may be in soluble form, or in solid phase. In particular, it may be bound to cell membranes or lipid vesicles, or to synthetic supports such as glass, plastic, polymers, filters, membranes, e.g., in the form of beads, columns, plates and the like.

The enzymes are preferably in isolated or purified form. Preferentially, enzymes of the invention are expressed, derived, secreted, isolated, or purified from a microorganism. The enzymes may be purified by techniques known per se in the art, and stored under conventional techniques. The enzymes may be further modified to improve, e.g., their stability or activity.

In another embodiment, the plastic product to be recycled is contacted with a microorganism that synthesizes and excretes the degrading enzyme. In the context of the invention the enzyme may be excreted in the culture medium or towards the cell membrane of the microorganism wherein said enzyme may be anchored.

Said microorganism may naturally synthesize the degrading enzyme, or it may be a recombinant microorganism, wherein a recombinant nucleotide sequence encoding the degrading enzyme has been inserted, using for example a vector.

For example, a nucleotide molecule encoding the degrading enzyme of interest is inserted into a vector, e.g., a plasmid, recombinant virus, phage, episome, artificial chromosome, or the like. Advantageously, the nucleotide molecule is under the control of a specific promoter. The vector is then transfected into host microorganisms to form recombinant microorganisms. The hosts are further cultured under culture conditions suitable for the hosts to thereby obtain recombinant cells containing the enzyme of the present invention. Culture conditions suitable for the hosts are well-known to those skilled in the art.

The nucleotide molecule of the invention can be in isolated or purified form, and made, isolated and/or manipulated by techniques known per se in the art, e.g., cloning and expression of cDNA libraries, amplification, enzymatic synthesis or recombinant technology.

The nucleotide molecule can also be synthesized in vitro by well-known chemical synthesis techniques. Nucleotide molecules of this invention may comprise additional nucleotide sequences, such as regulatory regions, i.e., promoters, enhancers, silencers, terminators, and the like that can be used to cause or regulate expression of the enzyme in a selected host cell or system.

The recombinant microorganisms may be used directly. Otherwise, or in addition, recombinant enzymes may be purified from the culture medium. Any commonly used separation/purification means, such as salting-out, gel filtration, hydrophobic interaction chromatography or ion exchange chromatography, may be used for this purpose.

In particular embodiments, microorganisms known to synthesize and excrete degrading enzymes may be used. For example *Aspergillus oryzae, Humicola insolens, Penicillium citrinum, Fusarium solani* and *Thermobifida cellulolysitica*, synthesizing and excreting a cutinase, may be used for degrading a plastic product containing PET. In the same way, *Candida antarctica, Thermomyces lanuginosus, Burkholderia* sp. and *Triticum aestivum* synthesize a lipase depolymerizing PET. *Amycolatopsis* sp. K104-1 and K104-2, *Tritirachium album* ATCC 22563, *Paenibacillus amylolyticus* TB-13, *Kibdelosporangium aridum* JCM 7912, *Saccharothrix waywayandensis* JCM 9114, *Amycolatopsis orientalis* IFO 12362, and *Actinomadura keratinilytica* T16-1 may be used for degrading a plastic product containing PLA. *Aspergillus fumigatus* NKCM1706 and *Bionectria ochroleuca* BFM-X1 may be used for degrading a plastic product containing PBS. *Thermomonospora fusca* K13g and K7a-3 and *Isaria fumosorosea* NKCM1712 may be used for degrading a plastic product containing PBAT. *Bjerkandera adusta* producing a manganese peroxidase may be used for degrading a plastic product containing PA.

According to the invention, several microorganisms and/or purified enzymes and/or synthetic enzymes may be used together or sequentially to depolymerize different kinds of polymers contained in the same plastic product or in different plastic products.

Advantageously, the microorganism of the invention exhibits a modified metabolism in order to prevent the consumption of the monomers obtained from the degraded polymer. For example, the microorganism is a recombinant microorganism, wherein the enzymes degrading said monomers have been deleted or knocked out. Otherwise, the process of the invention may be performed in a culture medium containing at least one carbon source usable by the microorganism so that said microorganism preferentially consumes this carbon source instead of the monomers.

Advantageously, the plastic product is contacted with a culture medium containing the microorganisms, glucose or the like as a carbon source, as well as a nitrogen source assimilable by the microorganisms, including an organic nitrogen source (e.g., peptone, meat extract, yeast extract, corn steep liquor) or an inorganic nitrogen source (e.g., ammonium sulfate, ammonium chloride). If necessary, the culture medium may further contain inorganic salts (e.g., sodium ion, potassium ion, calcium ion, magnesium ion, sulfate ion, chlorine ion, phosphate ion). Moreover, the medium may also be supplemented with trace components such as vitamins, oligo-elements and amino acids.

Recycling Process Parameters

According to the invention, a plastic product may be recycled by contacting said plastic product with a degrading enzyme targeting at least one polymer of said plastic product and/or a microorganism synthesizing and excreting such degrading enzyme.

The process of the invention is particularly useful for degrading a semi-crystalline polymer contained in a plastic product which contains said semi-crystalline polymer and eventually one or several other semi-crystalline and/or amorphous polymers and/or additives.

In a particular embodiment, the plastic product may be preliminarily treated to physically change its structure, so as to increase the surface of contact between the polymers and the enzymes. For example, the plastic product may be transformed to an emulsion or a powder, which is added to a liquid medium containing the microorganisms and/or enzymes. Otherwise, the plastic product may be mechanically ground, granulated, pelleted, etc. to reduce the shape and size of the material prior to being added to a liquid medium containing the microorganisms and/or enzymes.

The time required for degradation of a plastic product may vary depending on the plastic product itself (i.e., nature and origin of the plastic product, its composition, shape, etc.) and the type and amount of microorganisms/enzymes used, as well as various process parameters (i.e., temperature, pH, additional agents, etc.). One skilled in the art may easily adapt the process parameters to the plastic products and/or degrading enzymes.

Advantageously, the process is implemented at a temperature comprised between 20° C. and 80° C., more preferably between 25° C. and 60° C. Preferably, the temperature is maintained between 25° C. and 50° C. at least during the depolymerization step. More generally, the temperature is maintained below an inactivating temperature, which corresponds to the temperature at which the enzyme is inactivated and/or the microorganism no longer synthesizes the degrading enzyme. Surprisingly, the inventors discovered that the process of the invention may be implemented at a temperature below the Tg of the targeted polymer. According to the invention, the added amount of enzyme for the depolymerization step may be at least 0.005% by weight of plastic products, preferably at least 0.1% and more preferably at least 1%, and the added amount is advantageously at least 15% by weight of plastic products and more preferably at least 5%. Advantageously, the amount of degradation enzyme is in a range of 0.005% to 15% by weight of plastic product, preferably in a range of 0.1% to 10% and more preferably in a range of 1% to 5%.

The pH of the medium may be in the range of 4 to 10. Advantageously, the pH is adjusted according to the couple targeted polymer/enzyme for improving the process efficiency. More particularly, the pH is adjusted to be maintained at the optimal pH of the enzyme. Indeed, depolymerization of polyesters and polyamides produces acidic monomers that induce a pH decrease. An addition of a diluted alkali can be used to compensate for this acidification and maintain the pH at the optimal one.

In a particular embodiment, at least a lipophilic agent and/or hydrophilic agent is added to the medium for improving the depolymerization step. An inductor such as gelatin can be added to the medium to improve enzyme production. A surfactant such as Tween can be added to the medium to modify interface energy between the polymer and the enzyme or microorganism and improve degradation efficiency. An organic substance could be used to swell the polymer and increase its accessibility to the micro-organism or enzyme.

Advantageously, the process of the invention is performed without any degradation accelerator. In a particular embodiment, the process of the invention is performed in a degradation liquid containing only the degradation enzyme and water. In a particular embodiment, the process of the invention is performed without organic solvent.

The reaction time for depolymerization of at least one polymer of the plastic product is advantageously comprised between 5 and 72 hours. Such reaction time may allow the depolymerization to advance sufficiently, and will not be economically detrimental.

Treatment and Reuse of the Recovered Monomers

A mixture of monomers resulting from the depolymerization of the targeted polymers may be recovered at the end of the depolymerization step, sequentially or continuously. A single monomer or several different monomers may be recovered, depending on the depolymerized polymers and/or the recycled plastic products.

The monomers may be further purified, using any suitable purifying method and conditioned in a re-polymerizable form. Examples of purifying methods include stripping process, separation by aqueous solution, steam selective condensation, filtration and concentration of the medium after the bioprocess, separation, distillation, vacuum evaporation, extraction, electrodialysis, adsorption, ion exchange, precipitation, crystallization, concentration and acid addition dehydration and precipitation, nanofiltration, acid catalyst treatment, semi-continuous mode distillation or continuous mode distillation, solvent extraction, evaporative concentration, evaporative crystallization, liquid/liquid extraction, hydrogenation, azeotropic distillation process, adsorption, column chromatography, simple vacuum distillation and microfiltration, combined or not.

The re-polymerizable monomers may then be reused to synthesize polymers. Advantageously, polymers of same nature are repolymerized. However, it is possible to mix the recovered monomers with other monomers and/or oligomers, in order to synthesize new copolymers.

In a particular embodiment, repolymerization is conducted using a hydrolase in appropriate conditions for allowing a polymerization reaction. Initiators may be added to the monomer solution to favour the polymerization reaction. One skilled in the art may easily adapt the process parameters to the monomers and the polymers to by synthesized.

Further aspects and advantages of the invention will be disclosed in the following examples, which should be considered as illustrative and do not limit the scope of this application.

Examples

A. Aliphatic Polyester Recycling with an Enzyme

Plastic products containing aliphatic polyester such as PLA can be recycled thanks to the process of the invention. The present experiment shows the recovery of lactic acid by treating a plastic product constituted of semi-crystalline PLA with proteinase K.

Plastic Product and Pre-Treatment

PLA pellets were purchased from NaturePlast (PLLA 001) and were ground into powder with a particle size inferior to 500 µm using a Condux CUM 100 universal mill.

Differential Scanning calorimetry (DSC) tests were used in order to determine glass temperature (Tg) and crystallinity of polymers in plastic products, using a Q 100 TA-RCS 90 instrument under nitrogen atmosphere (50 mL/min) at a scanning rate of 10° C./min from −50° C. to 300° C. in aluminum pans on around 8 mg samples.

PLA powder had a Tg of 59° C. and was semi-crystalline with 14.9% of crystallinity.

Hydrolysis Reaction

The hydrolysis of the PLA powder was performed with proteinase K from *Tritirachium album* (Sigma) to recover lactic acid. The enzyme solution was prepared at the concentration of 10 mg/mL in Tris 20 mM with $CaCl_2$ 5 mM, pH 8. 20 mg PLA was treated by 200 μg proteinase K in Tris HCl 20 mM, pH 8 with 5 mM $CaCl_2$ at 37° C. in a final volume of 5 mL with magnetic stirring for 7 days.

In an experiment, pH was maintained at 8 (which corresponds to the optimal pH of proteinase K), with NaOH 0.5M during incubation to compensate for acidification by lactic acid production. Experiments were carried out in triplicate.

Controls were performed using i) PLA in buffer without enzyme and ii) enzyme in buffer without PLA.

Lactic Acid (LA) Assay

160 μL of reaction medium was sampled at each time of analysis. Samples were centrifuged at 16,000 g at 0° C. for 3 min. The supernatant for analysis was 0.45 μm filtered and 20 μL was injected in HPLC. The HPLC used was an Ultimate-3000 (Dionex, Thermo Scientific), with an autosampler thermostated to 10° C. and a column compartment thermostated to 50° C. For analysis of LA, an Aminex H+ HPX-87H column was used. Analysis was carried out with 5 mM $H_2SO_4$ as an eluent. The flow rate was set to 0.5 mL/min and the column was maintained at a temperature of 50° C. Detection of LA was performed with a variable wavelength detector at 220 nm. Quantification was possible considering standards prepared with L-lactic acid from Sigma (L-1750) dissolved in Tris HCl 20 mM, pH 8, in a 0-300 mM concentration range.

Results

PLA powder was hydrolyzed by proteinase K and lactic acid was recovered. No lactic acid was detected in controls. As shown in FIG. 1, the maximal concentration of lactic acid was obtained after 72 h of hydrolysis when pH adjustment was not realized. When pH was controlled, lactic acid concentration kept increasing up to 7 days of reaction. Maintaining the pH at 8 during the hydrolysis allowed the recovery of 5.87±0.92 mM LA at 72 h instead of 3.47±0.57 mM LA without pH adjustment. Accordingly, pH adjustment can thus be used as a parameter to modulate the process efficiency.

B. Aromatic Polyester Recycling with an Enzyme

Plastic products containing aromatic polyester such as PET and/or PTT can be recycled thanks to the process of the invention. The present experiments show the recovery of terephthalic acid by treating plastic products containing PET and/or PTT.

Plastic Products and Pre-Treatment

Different substrates were used:
PET film purchased from Goodfellow (ES 301445), thickness 0.25 mm, amorphous
PTT pellets purchased from DuPont (Sorona® 3301 NC010)
PET bottles (previously containing mineral water under trademark Cristalline®)

The PET film was cut into pieces of 10 mg (around 0.5 cm×1 cm). It was washed in three serial steps in order to remove any protein or lipid contaminants: in a first step it was washed with 5 g/L Triton-X 100, in a second step with 100 mM $Na_2CO_3$, and finally with deionized water. Each washing step was performed at 50° C. for 30 min. Then the PET film was dried with compressed air.

The PTT was ground into powder by using an SM-2000 cutting mill (Retsch) for 5 min and then sieved with an AS 200 siever (Retsch) for 10 min with an amplitude of 1.5 mm to obtain a powder of 1 mm.

The whole bottles were pre-treated to increase the surface of contact between the PET and the enzyme. They were mechanically ground into powders of different particle sizes by using an SM-2000 cutting mill (Retsch) for 5 min. The collected powder was then sieved with an AS 200 siever (Retsch) for 10 min with an amplitude of 1.5 mm to obtain 3 powders of respectively 1 mm, 500 μm and 250 μm particle size.

Differential Scanning calorimetry (DSC) tests were used in order to determine glass temperature (Tg) and crystallinity of polymers in plastic products, using a Q 100 TA-RCS 90 instrument under nitrogen atmosphere (50 mL/min) at a scanning rate of 10° C./min from −50° C. to 300° C. in aluminum pans on around 8 mg samples.

PTT and PET bottle powders had a Tg of 50.6° C. and 77.2° C. respectively and were semi-crystalline with 36% and 30% of crystallinity respectively.

Cutinase Production

*Thermobifida cellulosilytica* DSM44535 was obtained from the German Resource Centre for Biological Material (DSMZ, Germany). The strain was maintained on LB agar plates and cultivated in 500 mL shaking flasks (200 mL LB medium) at 37° C. and 160 rpm for 24 h. Cells were harvested by centrifugation at 3,200 g and 4° C. for 20 min.

Vector pET26b(+) (Novagen, Germany) was used for expression of cutinase THC_Cut2 from *Thermobifida cellulosytica* in *Escherichia coli* BL21-Gold (DE3) (Stratagene, Germany).

The gene Thc_cut2 coding for cutinase was amplified from the genomic DNA of *T. cellulosilytica* DSM44535 by standard polymerase chain reaction (PCR). On the basis of the known sequence of genes coding for cutinases from *T. fusca* YX (Genbank accession numbers YP_288944 and YP_288943,33) two primers were designed, 5'-CCCCCGCTCATATGGCCAACCCCTACGAGCG-3' (SEQ ID NO: 1—forward primer) and 5'-GTGT-TCTAAGCTTCAGTGGTGGTGGTGGTGGTGCTC-GAGTGCCAGGCACTGAGAG TAGT-3' (SEQ ID NO: 2—reverse primer), allowing amplification of the respective gene without signal peptide and introduction of the 6×His-Tag at the C-terminus of the cutinase. The designed primers included restriction sites NdeI and HindIII for cloning the gene into the vector pET26b(þ). The PCR was done in a volume of 50 μL with genomic DNA as template, 0.4 μM of each primer, 0.2 mM dNTP's, 5 units Phusion DNA polymerase (Finnzymes) and 1× reaction buffer provided by the supplier. The PCR was performed in a Gene Amp PCR 2200 thermocycler (Applied Biosystems, USA). 35 cycles were done, each cycle with sequential exposure of the reaction mixture to 98° C. (30 s, denaturation), 63° C. (30 s, annealing), and 72° C. (30 s, extension). Plasmids and DNA fragments were purified by Qiagen DNA purification kits (Qiagen, Germany). The purified amplified PCR products thus obtained were digested with restriction endonucleases NdeI and HindIII (New England Biolabs, USA), dephosphorylated with alkaline phosphatase (Roche, Germany) and ligated to pET26b(þ) with T4 DNA ligase (Fermentas, Germany) and transformed in *E. coli* BL21-Gold (DE3) in accordance with the manufacturer's instructions.

The sequence of the gene was determined by DNA sequencing using the primers 5'-GAGCGGATAACAATTC- CCCTCTAGAA-3' ((SEQ ID NO: 3) and 5'-CAGCTTC-CTTTCGGGCTTTGT-3' (SEQ ID NO: 4). DNA was sequenced as a custom service (Agowa, Germany). Analysis and handling of DNA sequences was performed with Vector NTi Suite 10 (Invitrogen, USA). Sequences of proteins were aligned using the Clustal W program (Swiss EMBnet node server). The nucleotide sequence of the isolated gene has been deposited in the GenBank database under accession number HQ147786 (Thc_cut2).

Freshly transformed *E. coli* BL21-Gold (DE3) cells were used to inoculate 20 mL of LB medium supplemented with 40 μg/mL kanamycin and cultivated overnight at 37° C. and 160 rpm. The overnight culture was used to inoculate 200 mL of LB medium with 40 μg/mL kanamycin to OD600=0.1 and incubated until an OD600=0.6-0.8 was reached. Afterwards the culture was cooled to 20° C. and induced with IPTG at a final concentration of 0.05 mM. Induction was done for 20 h at 20° C. and 160 rpm. The cells were harvested by centrifugation (20 min, 4° C., 3,200 g).

The cell pellet from 200 mL cell culture was resuspended in 30 mL binding buffer (20 mM NaH2PO4*2H2O, 500 mM NaCl, 10 mM imidazole, pH 7.4). The resuspended cells were sonicated with 30 s pulses three times under ice cooling (Vibra Cell, Sonics & Materials, Meryin-Satigny, Switzerland). The lysates were centrifuged (30 min, 4° C., 4,000 g) and filtered through a 0.2 μm membrane. The cell lysate was purified using an Akta purification system with HisTrap FF columns (elution buffer 20 mM $NaH_2PO_4$*$2H_2O$, 500 mM NaCl, 500 mM imidazole, pH 7.4). For characterization of cutinase the HisTag elution buffer was exchanged with 100 mM Tris HCl, pH 7.0 by the use of PD-10 desalting columns (GE Healthcare).

Protein concentrations were determined by the Bio-Rad protein assay kit (Bio-Rad Laboratories GmbH) and bovine serum albumin as protein standard. SDS-PAGE was performed corresponding to Laemmli (Laemmli, U. K. Nature 1970, 227 (5259), 680-685) and proteins were stained with Coomassie Brilliant Blue R-250.

All chemicals were of analytical grade from Sigma (Germany).

Hydrolysis Reaction

The hydrolysis of the plastic products was performed as follows. In each sample, 10 mg plastic product was incubated with 5 μM cutinase in 1 mL buffer $K_2HPO_4$/$KH_2PO_4$ 100 mM, pH 7.0 for 6 h to 72 h at 50° C. with 300 rpm shaking in Thermomixer Comfort (Eppendorf). All experiments were carried out in triplicate.

Controls were performed using i) plastic product in buffer without enzyme and ii) enzyme in buffer without plastic product.

Terephthalic Acid (TA) Assay

After enzymatic treatment, proteins were precipitated using 1:1 (v/v) absolute methanol (Merck) on ice. Samples were centrifuged (Hettich MIKRO 200 R, Tuttlingen, Germany) at 16,000 g at 0° C. for 15 min. The supernatant for measurement was brought to an HPLC vial and acidified by adding 3.5 μL of 6N HCl. The HPLC used was a DIONEX P-580 pump (Dionex Corporation, Sunnyvale, USA), with an ASI-100 automated sample injector and a PDA-100 photodiode array detector. For analysis of TA, an RP-C18 reversed phase column (Discovery HS-C18, 5 μm, 150×4.6 mm with precolumn, Supelco, Bellefonte, USA) was used. Analysis was carried out with 60% water, 10% 0.01N $H_2SO_4$ and 30% methanol as an eluent, gradual (15 min) to 50% methanol and 10% acid, gradual (20 min) to 90% methanol and acid, staying 2 min and then gradual to starting position, 5 min post run. The flow rate was set to 1 mL/min and the column was maintained at a temperature of 25° C. The injection volume was 10 μL. Detection of TA was performed with a photodiode array detector at the wavelength of 241 nm. Quantification was possible using standards of terephthalic acid (Merck code: 800762) diluted in 1:1 buffer:MetOH with different concentrations (1, 5, 10, 50, 100, 250 μM) prepared in the same way as the samples.

Results

The present experiments showed that plastic products formulated with polymers and additives can be recycled using the process of the invention. Furthermore, in order to improve the monomer recovery, a mechanical pre-treatment of the plastic product may be advantageously performed which increases the surface contact between plastic product and enzyme.

Figure 2:
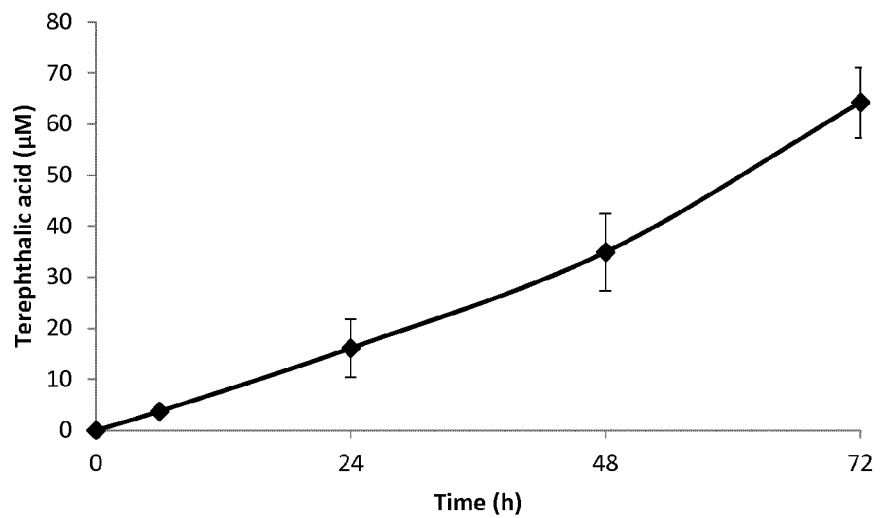
FIG. 2 shows that a polyethylene terephthalate contained in a plastic product may be hydrolyzed by the process of the invention and terephthalic acid monomers may be recovered.

More particularly, the PET film was hydrolyzed by cutinase for 72 h to obtain TA. The longer the time of the reaction was, the more TA was produced (FIG. 2).

The PTT was hydrolyzed by cutinase: 4.087±0.122 μM TA was obtained in 24 h.

The PET bottle in the form of powder with particle size of 1 mm was hydrolyzed by cutinase: 7.301±0.162 μM TA was obtained in 24 h. Accordingly, the process of the invention can also be applied to PET plastic formulated with additives, such as the ones found in plastic wastes.

Figure 3:
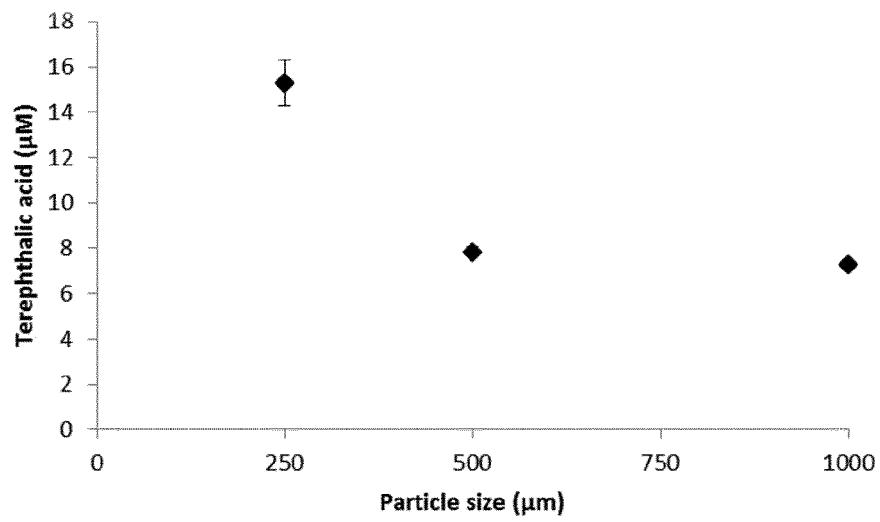
FIG. 3 shows the impact of the particle size of a PET plastic product on the efficiency of the process of the invention.

Different size particles of PET bottle powder were hydrolyzed by cutinase to obtain TA in 24 h. Reducing the particle size by mechanical grinding improved the enzyme efficiency to produce more TA: 15.296±1.012 μM TA with 250 μm particle size instead of 7.301±0.162 μM TA with 1 mm particle size (FIG. 3).

C. Polyamide Recycling with an Enzyme

Plastic products containing polyamides can be recycled thanks to the process of the invention. The present example shows the recovery of adipic acid by treating plastic products constituted of PA with a polyamidase expressed by a recombinant strain of *Escherichia coli*.

Plastic Product and Pre-Treatment

Commercial polyamide fabric is purchased from Rhodia (Switzerland): PA6,6, 63 g/m², cut into pieces of 3 cm×3 cm. It is washed with $Na_2HPO_4$, $2H_2O$, 5 mM for 30 min in order to remove the surface finishes.

Polyamidase Production

The gene coding for the polyamidase from *Nocardia farcinica* IFM 10152 (NCBI accession number NC 006361) is codon optimized for expression in *Escherichia coli* (GeneArt AG, Germany) and fused to a nucleotide sequence allowing introduction of the 6×HisTag at the C-terminus of the protein. The gene is digested with restriction endonucleases NdeI and HindIII (New England Biolabs, USA), dephosphorylated with alkaline phosphatase (Roche, Germany), purified, ligated with T4 DNA ligase (Fermentas, Germany) to pET26b(+) (Novagen, Merck KGaA, Germany) and transformed in *E. coli* BL21-Gold (DE3) in accordance with the manufacturer's instructions. The Plasmid Mini Kit from Qiagen (Germany) is used to prepare plasmid DNA. Plasmids and DNA fragments are purified by Qiagen DNA purification kits (Qiagen, Germany). Freshly transformed cells are used to inoculate 20 mL LB medium supplemented with 40 μg/mL kanamycin. The culture is grown overnight on a rotary shaker at 30° C. and 160 rpm. Then 1 mL of the overnight culture is transferred to a 500 mL shaking flask containing 200 mL of the same liquid medium and incubated at 30° C. until an optical density (600 nm) between 0.6 and 0.8 is reached. The culture is cooled down to 20° C. and induced with IPTG at a final concentration of 0.05 mM. The induced culture is incubated overnight at 20° C. and 160 rpm. The cells are harvested by centrifugation (3200 g, 4° C., 20 min).

Purification is done by gravity flow chromatography using Ni-NTA Sepharose according to the manufacturer's protocol (IBA GmbH, Germany) with the exception of using 100 mM imidazole for elution of the protein. For characterization of polyamidase the HisTag elution buffer was exchanged with 100 mM Tris HCl, pH 7.0 by the use of PD-10 desalting columns (Amersham Biosciences).

Protein concentrations are determined by the Uptima BC Assay protein quantification kit from Interchim (France) and bovine albumin as protein standard. SDS-PAGE is performed according to Laemmli (Laemmli, U. K. Nature 1970, 227 (5259), 680-685) and proteins are stained with Coomassie Brillant Blue R-250.

Hydrolysis Reaction

Polyamide fabrics are incubated in 100 mL of citrate phosphate buffer (25 mM, pH 5.0) with 2 mg/mL of polyamidase. After the hydrolysis, the fabrics are washed with sodium carbonate (9.4 mM, pH 9.5) followed by four rinsing steps with distilled water to remove adsorbed proteins. All the steps are done at 30° C. for 30 min. After the last step, the fabrics are dried at room temperature overnight.

Controls are performed using i) plastic product in buffer without enzyme and ii) enzyme in buffer without plastic product.

Adipic Acid Assay

After enzymatic treatment, proteins are precipitated using Carrez precipitation. Therefore the pH of the samples has to be between 4 and 6. 2% of solution C1 (0.252 M K4[Fe (CN)6], 3 $H_2O$) are added to the samples, and after vortexing and incubation for 1 minute, 2% of solution C2 (1 mM $ZnSO_4$, 7 $H_2O$) are added. After vortexing and incubation for 5 minutes the samples are centrifuged (30 minutes, 16,000 g, 25° C.). The supernatants are filtered through a 0.45 µm filter membrane directly into glass vials for HPLC analysis (Hewlett Packard Series 1100, Refractive Index Detector: Agilent Series 1100). An ION-300 column (Transgenomic, Inc.) is used, the flow is set to 0.1 mL/min and 0.01N $H_2SO_4$ is used as a mobile phase. The temperature is set to 45° C. and the injection volume is 40 µL. Detection is realized at a wavelength of 220 nm. Calibration is achieved using adipic acid standard solutions.

Results

The PA is hydrolyzed by polyamidase: 9.4 µM adipic acid is obtained in 48 h.

D. Aliphatic Polyester Recycling with a Recombinant Microorganism

Plastic products containing aliphatic polyester such as PLA can be recycled thanks to the process of the invention with an enzyme like in example A as well as with a recombinant microorganism expressing and excreting a depolymerase, with a modified metabolism preventing the consumption of the resulting monomers. The modified metabolism can be obtained either by gene deletion or by gene disruption or knock-out. The present experiment shows the recovery of lactic acid by treating plastic products constituted of semi-crystalline PLA with a recombinant strain of *Lactococcus lactis* or *Escherichia coli*. The strain modifications shown in the examples can also be performed on other microorganisms.

Plastic Product and Pre-Treatment

PLLA pellets are purchased from NaturePlast (PLLA 001) and are ground into powder with a particle size inferior to 500 µm using a Condux CUM 100 universal mill.

Differential Scanning calorimetry (DSC) tests are used in order to determine glass temperature (Tg) and crystallinity of polymers in plastic products, using a Q 100 TA-RCS 90 instrument under nitrogen atmosphere (50 mL/min) at a scanning rate of 10° C./min from −50° C. to 300° C. in aluminum pans on around 8 mg samples.

PLLA powder has a Tg of 59° C. and is semi-crystalline with 14.9% of crystallinity. Its mass characteristics are Mw 71000 g/mol and Mn 45000 g/mol determined by SEC.

*L. lactis* Construction

The wild-type strain of *L. lactis* MG1363 is recombined with the gene pld coding for a PLA depolymerase from *Amycolatopsis* sp. K104-1 (SEQ ID NO: 5) (Nakamura et al., 2001, Appl. Environ. Microbiol. 67:345-353), according to the classical method described in Molecular Cloning: A Laboratory Manual, Cold Spring Harbor Laboratory Press, Cold Spring Harbor, N.Y. Therefore, a homologous recombination was achieved in a pNZ8048 plasmid (Kuipers et al., 1998, J. Biotechnol. 64:15-21). The recombinant plasmid with the pld gene is called "pNZ-pld". The *L. lactis* strain is transformed by the pNZ-pld plasmid by electroporation according to classical method described in Ho et al., 1995, Transformation of *Lactococcus* by electroporation, Methods Mol. Biol. 47:195-199. The recombinant *L. lactis* strain is called "MG1363-pNZ-pld". The negative control corresponds to the *L. lactis* MG1363 strain transformed with an empty pNZ8048 plasmid.

*E. coli* Construction

*E. coli* K12-MG1655 contains 3 lactate dehydrogenases (LDHs). One LDH is specific for the D-lactate isomer. Another LDH converts pyruvate to lactate under anaerobic conditions. The last LDH is specific for the L-lactate isomer and allows growth on this substrate (Haugaard, N. (1959) D- and L-lactic acid oxidases of *Escherichia coli*. Biochim Biophys Acta 31, 66-77; Kline, E. S. & Mahler, E. R. (1965). The lactic acid dehydrogenases of *Escherichia coli*. Ann N Y Acad Sci 119, 905-917). For the recycling process, the expression of this last LDH must be suppressed in order to recover lactic acid without any consumption of it.

The disruption of the lldD gene (SEQ ID NO: 6) coding for LDH in *E. coli* allows suppression of lactic acid consumption. To disrupt the lldD gene, the ampicillin (Amp) resistance amp gene from the pKD4 plasmid is inserted in the sequence of the lldD gene by homologous recombination as described by Datsenko and Wanner (2000), with primers DlldD-F (SEQ ID NO: 7) and DlldD-R (SEQ ID NO: 8) with a sequence homologous to the sequence of the lldD gene and a sequence homologous to the amp gene. The Amp-resistant transformants are then selected and the chromosomal structure of the mutated loci is verified by PCR analysis with the appropriate primers homologous to upstream and downstream sequences of the lldD gene (SEQ ID NO: 9 and SEQ ID NO: 10) and by DNA sequencing.

Then *E. coli* is recombined with the gene pld coding for a PLA depolymerase from *Amycolatopsis* sp. K104-1 (SEQ ID NO: 5; Nakamura et al., 2001, Appl. Environ. Microbiol. 67:345-353), according to the classical method described in Molecular Cloning: A Laboratory Manual, Cold Spring Harbor Laboratory Press, Cold Spring Harbor, N.Y. Therefore, a homologous recombination is achieved in the pNZ8048 plasmid (Kuipers et al., 1998, J. Biotechnol. 64:15-21). The recombinant plasmid with the pld gene is called "pNZ-pld". The disrupted lldD *E. coli* strain is transformed by the pNZ-pld plasmid. The recombinant disrupted *E. coli* strain is called "K12DlldD-pNZ-pld". The negative control corresponds to the *E. coli* strain transformed with an empty pNZ8048 plasmid.

Hydrolysis Reaction

The 2 strains of *L. lactis*, MG1363-pNZ-pld and MG1363-pNZ, and the 2 strains of *E. coli*, K12DlldD-pNZ-pld and K12DlldD-pNZ8048, are cultivated in bioreactors of 2 L in R2 medium at 30° C. Each culture is subdived into 2 sub-cultures: lot 1 without PLLA and lot 2 with 0.1% (m/v) PLLA.

Lactic Acid Assay 2 mL of each reaction medium are sampled after 2 days of culture. Samples are centrifuged at 16,000 g at 0° C. for 3 min. The supernatant for analysis is 0.45 μm filtered and 20 μL are injected in HPLC. The HPLC used is an Ultimate-3000 (Dionex, Thermo Scientific), with an autosampler thermostated to 10° C. and a column compartment thermostated to 50° C. For analysis of LA, an Aminex H+ HPX-87H column is used. Analysis is carried out with 5 mM $H_2SO_4$ as an eluent. The flow rate is set to 0.5 mL/min and the column is maintained at a temperature of 50° C. Detection of LA is performed with a variable wavelength detector at 220 nm. Quantification is possible considering standards prepared with L-lactic acid from Sigma (L-1750) dissolved in Tris HCl 20 mM, pH 8, in a 0-300 mM concentration range.

Results

Only the recombinant *L. lactis* strain MG1363-pNZ-pld and the recombinant disrupted *E. coli* strain K12DlldD-pNZ-pld expressing a PLA depolymerase produce lactic acid from PLA. The lactate dehydrogenase disruption allows recovery of lactic acid without consumption by the strain.

The invention claimed is:

1. A method for recycling at least one plastic product comprising at least partially semi-crystalline polyethylene terephthalate (PET) and at least one other additive, the method comprising:
providing, without sorting, a mixture of plastic products coming from plastic waste collection and comprising said at least one plastic product;
selecting a degrading enzyme suitable for degrading the at least partially semi-crystalline PET of the at least one plastic product;
depolymerizing the at least partially semi-crystalline PET of the plastic product to monomers by contacting the at least one plastic product with the degrading enzyme;
recovering the resulting monomers; and
synthesizing polymers from the recovered monomers,
wherein the depolymerizing step is conducted in a liquid medium whose pH is adjusted to be maintained at the optimal pH of the degrading enzyme during all of the depolymerizing step.

2. The method of claim 1, wherein the enzyme is a cutinase (EC 3.1.1.74).

3. The method of claim 1, wherein the step of depolymerizing by the enzyme comprises contacting the plastic product with at least one microorganism expressing and excreting said enzyme.

4. The method of claim 3, wherein the microorganism is a recombinant microorganism expressing and excreting a recombinant degrading enzyme.

5. The method of claim 1, wherein the plastic product is pretreated prior to degradation.

6. The method of claim 5, wherein the pretreatment includes mechanical/physical modification of the plastic product.

7. The method of claim 6, wherein the pretreatment comprises grinding of the plastic product.

8. The method of claim 1, wherein at least one lipophilic and/or hydrophilic agent is used together with said enzyme.

9. The method of claim 1, wherein the plastic product further comprises at least one additional polymer chosen among amorphous and/or semi-crystalline polyesters and amorphous and/or semi-crystalline polyamides.

10. The method of claim 9, wherein the at least one additional polyester is selected from polytrimethylene terephthalate (PTT), polybutylene terephthalate (PBT), polyethylene isosorbide terephthalate (PEIT), polylactic acid (PLA), poly(L-lactic acid) (PLLA), poly(D-lactic acid) (PDLA), poly(D,L-lactic acid) (PDLLA), stereocomplex PLA (scPLA), polyhydroxy alkanoate (PHA), poly(3-hydroxybutyrate) (P(3HB)/PHB), poly(3-hydroxyvalerate) (P(3HV)/PHV), poly(3-hydroxyhexanoate) (P(3HHx)), poly (3-hydroxyoctanoate) (P(3HO)), poly(3-hydroxydecanoate) (P(3HD)), poly(3-hydroxybutyrate-co-3-hydroxyvalerate) (P(3 HB-co-3HV)/PHBV), poly(3-hydroxybutyrate-co-3-hydroxyhexanoate) (P(3HB-co-3HHx)/(PHBHHx)), poly(3-hydroxybutyrate-co-5-hydroxyvalerate) (PHB5HV), poly (3-hydroxybutyrate-co-3-hydroxypropionate) (PHB3HP), polyhydroxybutyrate-co-hydroxyoctonoate (PHBO), polyhydroxybutyrate-co-hydroxyoctadecanoate (PHBOd), poly (3-hydroxybutyrate-co-3-hydroxyvalerate-co-4-hydroxybutyrate) (P(3HB-co-3HV-co-4HB)), polybutylene succinate (PBS), polybutylene succinate adipate (PBSA), polybutylene adipate terephthalate (PBAT), polyethylene furanoate (PEF), Polycaprolactone (PCL), poly(ethylene adipate) (PEA) and blends/mixtures of these materials.

11. The method of claim 9, wherein the polyamide is selected from polyamide-6, poly(β-caprolactam), polycaproamide (PA6), polyamide-6,6, poly(hexamethylene adipamide) (PA6,6), poly(11-aminoundecanoamide) (PA11), polydodecanolactam (PA12), poly(tetramethylene adipamide) (PA4,6), poly(pentamethylene sebacamide) (PA5, 10), poly(hexamethylene azelaamide) (PA6,9), poly(hexamethylene sebacamide) (PA6,10), poly(hexamethylene dodecanoamide) (PA6,12), poly(m-xylylene adipamide) (PAMXD6), polyhexamethylene adipamide/polyhexamethylene terephthalamide copolymer (PA66/6T), polyhexamethylene adipamide/polyhexamethylene isophthalamide copolymer (PA66/6I) and blends/mixtures of these materials.

12. The method of claim 1, wherein said at least one plastic product comprises at least two different plastic polymers and the at least two different plastic polymers are depolymerized sequentially.

13. The method of claim 1, wherein the mixture of plastic products comprises at least two plastic products, and the at least two plastic products coming from plastic waste collection are recycled, simultaneously or sequentially.

14. The method of claim 1, wherein the depolymerizing step is performed at a temperature below the Tg of the targeted polymer.

15. The method of claim 1, wherein the depolymerizing step is performed at a temperature between 20° C. and 80° C.

16. The method of claim 1, wherein the depolymerizing step is performed at a temperature between 25° C. and 60° C.

17. The method of claim 1, wherein the other additive of the plastic product is selected from a plasticizer, mineral filler and organic filler.

18. The method of claim 1, wherein the semi-crystalline PET has at least about 14.9% crystallinity.

19. The method of claim 1, wherein the semi-crystalline PET has at least about 30% crystallinity.

20. The method of claim 1, wherein the mixture of plastic products is selected from plastic bottles, plastic bags, plastic packaging and textile waste.

21. A method for producing terephthalic acid from a mixture of plastic products coming from plastic waste collection, wherein at least one plastic product comprises at least partially semi-crystalline polyethylene terephthalate (PET) and at least one or several other additives, wherein the method comprises the steps of:
  providing a mixture of plastic products coming from plastic waste collection and comprising said at least one plastic product;
  selecting a degrading enzyme suitable for degrading the semi-crystalline PET of the at least one plastic product;
  depolymerizing the semi-crystalline PET of the at least one plastic product to terephthalic acid by contacting the at least one plastic product with the degrading enzyme; and
  recovering the resulting terephthalic acid,
  wherein the depolymerizing step is conducted in a liquid medium whose pH is adjusted to be maintained at the optimal pH of the degrading enzyme during all of the depolymerizing step.

22. The method of claim 21, wherein at least two plastic products coming from plastic waste collection comprising semi-crystalline polyethylene terephthalate (PET) are recycled, simultaneously or sequentially.

23. The method of claim 1, further comprising synthesizing PET from the recovered monomers and, optionally, fabricating new plastic products from the PET synthesized from the recovered monomers.

* * * * *

```
                        SEQUENCE LISTING

<160> NUMBER OF SEQ ID NOS: 10

<210> SEQ ID NO 1
<211> LENGTH: 31
<212> TYPE: DNA
<213> ORGANISM: artificial sequence
<220> FEATURE:
<223> OTHER INFORMATION: primer

<400> SEQUENCE: 1
cccccgctca tatggccaac ccctacgagc g                              31

<210> SEQ ID NO 2
<211> LENGTH: 59
<212> TYPE: DNA
<213> ORGANISM: artificial sequence
<220> FEATURE:
<223> OTHER INFORMATION: primer

<400> SEQUENCE: 2
gtgttctaag cttcagtggt ggtggtggtg gtgctcgagt gccaggcact gagagtagt    59

<210> SEQ ID NO 3
<211> LENGTH: 26
<212> TYPE: DNA
<213> ORGANISM: artificial sequence
<220> FEATURE:
<223> OTHER INFORMATION: primer

<400> SEQUENCE: 3
gagcggataa caattcccct ctagaa                                    26

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4
cagcttcctt tcgggctttg t                                         21

<210> SEQ ID NO 5
<211> LENGTH: 717
<212> TYPE: DNA
<213> ORGANISM: Amycolatopsis sp. K104-1

<400> SEQUENCE: 5
gtgaaattcg gcaagttcgt cctgctggcc gcgagcaccg cactggccgt cgtcggcctc    60
```

| ggcggtccgg cggccgccga cagcaccccg caggcccagc cgtcgatcat cggtggcagc | 120 |
| aacgccacca gtggcccctg gcggccggg ctgttcgtca acggccggca gaactgcacc | 180 |
| gcgacgatca tcgccccgca gtacatcctc accgccaagc actgcgtcag cagctccggc | 240 |
| acctacacgt tccgcatcgg cagcctggac cagacgagcg gcggcacgat ggccaccggc | 300 |
| tccacgatca cgcgctaccc gggctccgcc gacctggcga tcgtccggct caccacctcg | 360 |
| gtgaacgcca cctactcgcc actcggcagc gtcggtgacg tttcggtcgg ccagaacgtc | 420 |
| tcggtctacg gctggggcgc gaccagccag tgcggctccg agatcaactg ccagtcgcgg | 480 |
| tacctgaagg tcgcgacggt gcgggtgaac tcgatcagct gcagcgacta caccggcggc | 540 |
| gtcgccgtgt gcgcgaaccg cgtcaacggc atcaccgccg gcggcgactc cggcggcccg | 600 |
| atgttcgctt ccggccgcca ggtcggccgtc gcgtcgacca cgaccggggt gaacaacacg | 660 |
| gcgtacacca acatcacgcg ttatcgcagc tggatttcgc aggtggcggg cgtctga | 717 |

<210> SEQ ID NO 6
<211> LENGTH: 1191
<212> TYPE: DNA
<213> ORGANISM: E. Coli

<400> SEQUENCE: 6

| atgattattt ccgcagccag cgattatcgc gccgcagcgc aacgcattct gccgccgttc | 60 |
| ctgttccact atatggatgg tggtgcatat tctgaataca cgctgcgccg caacgtggaa | 120 |
| gatttgtcag aagtggcgct gcgccagcgt attctgaaaa acatgtccga cttaagcctg | 180 |
| gaaacgacgc tgtttaatga aaattgtcg atgccggtgg cactggctcc ggtgggtttg | 240 |
| tgtggcatgt atgcgcgtcg tggcgaagtt caggcagcca agcggcgga cgcgcatggt | 300 |
| attccgttta ctctctcgac ggtttccgtt tgcccgattg aagaagtcgc gccagccatc | 360 |
| aagcgcccaa tgtggttcca gctttatgta ctgcgcgatc gcggctttat gcgtaacgcg | 420 |
| ctggagcgag caaaagcagc gggttgttcg acgctggttt tcaccgtgga tatgccgaca | 480 |
| ccgggcgcac gctaccgtga tgcgcattca ggtatgagcg gcccgaacgc ggcaatgcgc | 540 |
| cgctacttgc aagcggtgac acatccgcaa tgggcgtggg atgtgggcct gaacggtcgt | 600 |
| ccacatgatt taggtaatat ctcagcttat ctcggcaaac cgaccggact ggaagattac | 660 |
| atcggctggc tggggaataa cttcgatccg tccatctcat ggaaagacct tgaatggatc | 720 |
| cgcgatttct gggatggccc gatggtgatc aaagggatcc tcgatccgga agatgcgcgc | 780 |
| gatgcagtac gttttggtgc tgatggaatt gtggtttcta accacggtgg ccgccagctg | 840 |
| gacggtgtac tctcttccgc ccgtgcactg cctgctattg cagatgcggt gaaaggtgat | 900 |
| atagccattc tggcggatag cggaattcgt aacgggcttg atgtcgtgcg tatgattgcg | 960 |
| ctcggtgccg acaccgtact gctgggtcgt gctttcttgt atgcgctggc aacagcgggc | 1020 |
| caggcgggtg tagctaacct gctaaatctg atcgaaaaag atgaaagt ggcgatgacg | 1080 |
| ctgactggcg cgaaatcgat cagcgaaatt acgcaagatt cgctggtgca ggggctgggt | 1140 |
| aaagagttgc ctgcggcact ggctcccatg gcgaaaggga atgcggcata g | 1191 |

<210> SEQ ID NO 7
<211> LENGTH: 40
<212> TYPE: DNA
<213> ORGANISM: artificial sequence
<220> FEATURE:
<223> OTHER INFORMATION: primer

<400> SEQUENCE: 7

```
atgattattt ccgcagccag catatgaata tcctccttag         40
```

<210> SEQ ID NO 8
<211> LENGTH: 40
<212> TYPE: DNA
<213> ORGANISM: artificial sequence
<220> FEATURE:
<223> OTHER INFORMATION: primer

<400> SEQUENCE: 8

```
gctttccctt acgccgtatc tgtaggctgg agctgcttcg         40
```

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9

```
cattcgaggg agaaaaacgc                               20
```

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10

```
agcaaacgcg ggggagtggg                               20
```